United States Patent
Jiang et al.

(10) Patent No.: US 11,771,805 B2
(45) Date of Patent: Oct. 3, 2023

(54) INJECTABLE IN SITU PORE-FORMING HYDROGEL SYSTEM AND PREPARATION METHOD AND USE THEREOF

(71) Applicant: Shanghai Ninth People's Hospital, Shanghai JiaoTong University School of Medicine, Shanghai (CN)

(72) Inventors: Xinquan Jiang, Shanghai (CN); Wenjie Zhang, Shanghai (CN); Yanmei Tang, Shanghai (CN); Sihan Lin, Shanghai (CN)

(73) Assignee: Shanghai Ninth People's Hospital, Shanghai JiaoTong University School of Medicine, Shanghai (CN)

( * ) Notice: Subject to any disclaimer, the term of this patent is extended or adjusted under 35 U.S.C. 154(b) by 0 days.

(21) Appl. No.: 17/636,900

(22) PCT Filed: Jul. 7, 2020

(86) PCT No.: PCT/CN2020/100635
§ 371 (c)(1),
(2) Date: Jun. 27, 2022

(87) PCT Pub. No.: WO2021/031726
PCT Pub. Date: Feb. 25, 2021

(65) Prior Publication Data
US 2022/0339320 A1    Oct. 27, 2022

(30) Foreign Application Priority Data
Aug. 22, 2019   (CN) ......................... 201910780496.1

(51) Int. Cl.
*A61L 27/52*    (2006.01)
*A61L 27/04*    (2006.01)
(Continued)

(52) U.S. Cl.
CPC .............. *A61L 27/52* (2013.01); *A61L 27/047* (2013.01); *A61L 27/3834* (2013.01);
(Continued)

(58) Field of Classification Search
None
See application file for complete search history.

(56) References Cited

U.S. PATENT DOCUMENTS

2019/0015553 A1    1/2019   Lee et al.

FOREIGN PATENT DOCUMENTS

CN    102552986 Y    7/2012
CN    103237565 Y    8/2013
(Continued)

OTHER PUBLICATIONS

Tang et al. "In situ gas foaming based on magnesium particle degradation: A novel approach to fabricate injectable macroporous hydrogels", Biomaterials, vol. 232, Dec. 2019, 119727. (Year: 2019).*

Kim et al. "Mesenchymal stem cells differentiation in porous alginate hydrogels constructed with magnesium oxide as porogen", Korean Polymer Society Conference Abstracts, 2015, 1PS-293. (Year: 2015).*

(Continued)

*Primary Examiner* — Carlos A Azpuru
*Assistant Examiner* — Casey S Hagopian

(57) ABSTRACT

An injectable in situ pore-forming hydrogel system and its preparation method and use are provided. The injectable in situ pore-forming hydrogel system uses an injectable hydrogel as a continuous base phase, and isolated live cells and magnesium particles are distributed in the continuous base phase, where the injectable hydrogel is a precursor or prepolymer of hydrogel, which can form hydrogel by cross-linking. The injectable in situ pore-forming hydrogel system can be used to create pores while the gel encapsulates live cells, which makes use of both the injectability and porous structures of hydrogel, which is important for the repair of cavitary, surgically difficult and irregularly defective tissues;

(Continued)

meanwhile, magnesium particles generate magnesium ions after the former undergoes gas production and degradation, which can improve the bioactivity of the gel and aid in tissue repair.

9 Claims, 3 Drawing Sheets

(51) Int. Cl.
    *A61L 27/38*     (2006.01)
    *A61L 27/56*     (2006.01)

(52) U.S. Cl.
    CPC ........... *A61L 27/56* (2013.01); *A61L 2400/06* (2013.01); *A61L 2430/02* (2013.01)

(56) References Cited

FOREIGN PATENT DOCUMENTS

| CN | 107964105 A | 4/2018 | |
|---|---|---|---|
| CN | 110478532 | 11/2019 | |
| WO | WO-2019046834 A1 * | 3/2019 | ........... A61K 31/728 |

OTHER PUBLICATIONS

Translation of Kim et al. "Mesenchymal stem cells differentiation in porous alginate hydrogels constructed with magnesium oxide as porogen", Korean Polymer Society Conference Abstracts, 2015, 1PS-293. (Year: 2015).*

Tang, Yanmei, "In situ gas foaming based on magnesium particle degradation: A novel approach to fabricate injectable macroporous hydrogels", «Biomaterials», vol. 232, Dec. 24, 2019, Netherlands ISSN:0142-9612, sections 2-3.

* cited by examiner

INJECTABLE IN SITU PORE-FORMING HYDROGEL SYSTEM AND PREPARATION METHOD AND USE THEREOF

CROSS REFERENCE TO RELATED APPLICATION

This is a Sect. 371 National Stage of PCT International Application No. PCT/CN2020/100635, filed on Jul. 7, 2020, which claims the benefit of priority to Chinese Patent Application No. CN 2019107804961, entitled "INJECTABLE IN SITU PORE-FORMING HYDROGEL SYSTEM AND PREPARATION METHOD AND USE THEREOF", filed with CNIPA on Aug. 22, 2019, the disclosure of which is incorporated herein by reference in its entirety.

FIELD OF TECHNOLOGY

The present disclosure relates to the field of hydrogel, in particular to a bioactive hydrogel and its preparation method.

BACKGROUND

Hydrogel has been widely used in the field of tissue engineering and regenerative medicine as a three-dimensional culture and delivery system for live cells due to its bionic structure highly similar to natural extracellular matrices. Compared with traditional tissue engineering scaffold materials, injectable hydrogel systems can transport stem cells to defects under minimally invasive conditions with easy and efficient operation. However, it has been reported that only 1-20% of the stem cells implanted along with hydrogel in the defects can survive in the host. This phenomenon is due to the polymeric network structure of hydrogel, and the polymeric network structure retains a large amount of water and has no interpenetrating porous structure. The lack of interpenetrating porous structures hinders rapid diffusion of nutrients and growth of surrounding blood vessels, and therefore greatly affects the bioactivity and survival status of the loaded cells. The above-mentioned problem has become a major obstacle to applying hydrogel in tissue regeneration.

Hydrogel with a porous structure can be prepared by a traditional template method, freeze-drying method, phase separation method, etc. However, the gel prepared by these methods are all of a preformed scaffold type, which lose the injectability that most gels have, limiting its scope of applications, while some methods require harsh conditions and complicated process, which are unfavorable to live cells and don't allow for pore formation while loading cells. Patent Application No. PCT/US2011/055174 discloses a method of using oxidized alginate microspheres as porogens, in which hydrogel containing both live cells and porogens is injected into the body and the microspheres degrade, leaving vacuolated pores in the gel. This "in situ pore formation" method allows the gel to create a porous structure directly within the injected site, thus making the gel both injectable and porous. However, degradation of the microspheres in this method requires a lengthy infiltration of tissue fluid, which leads to uneven degradation of the microspheres inside the gel and unconnected pores under time-limited conditions. Such uneven degradation is not conducive to the survival of cells deep in the gel and rapid vascularization. This porous gel was also reported to be ineffective in promoting bone regeneration. In addition, there is no other method to prepare porous structures in injectable hydrogel containing live cells.

SUMMARY

An injectable in situ pore-forming hydrogel system and preparation method and use thereof are provided.

The present disclosure provides an injectable in situ pore-forming hydrogel system, which uses an injectable hydrogel as a continuous base phase, isolated live cells and magnesium particles are distributed in the continuous base phase, and the injectable hydrogel is a precursor or prepolymer of a hydrogel, which can form the hydrogel by crosslinking.

In one embodiment of the present disclosure, the injectable hydrogel is a precursor or prepolymer of a hydrogel selected from the group consisting of alginate, gelatin, agarose, chitosan, collagen, silk fibroin, cellulose, glucose, hyaluronic acid, chondroitin sulfate, polyvinyl alcohol, polyethylene glycol, and their derivatives.

In one embodiment of the present disclosure, the isolated cells are one or more of mesenchymal stem cells, embryonic stem cells, induced multifunctional cells, and adult cells.

In one embodiment of the present disclosure, the isolated live cells can be obtained by a tissue block adherence method, mechanical separation method, digestion separation method, suspension culture method, flow cytometry sorting method, or immunomagnetic bead sorting method.

In one embodiment of the present disclosure, the concentration of cells in the injectable hydrogel system is $10^6$-$10^7$ cells/m L.

In one embodiment of the present disclosure, the average particle size of the magnesium particles is from 20 μm to 100 μm. The maximum particle size of the magnesium particles is 150 μm. The magnesium particles include flake particles, spherical particles obtained by a mechanical grinding method, atomization method, reduction method, electrolysis method, etc. A mass fraction of the magnesium element in the magnesium particles is above 99%. Preferably, the mass fraction of the magnesium element in the magnesium particles is above 99.98%.

In one embodiment of the present disclosure, 0.2 mg to 2.0 mg of magnesium particles are added to one milliliter of the injectable in situ pore-forming hydrogel system.

The present disclosure also discloses a method of preparing an injectable in situ pore-forming hydrogel system as described above, which includes mixing the injectable hydrogel, isolated live cells, and magnesium particles.

The present disclosure also discloses a use of the injectable in situ pore-forming hydrogel system as described above, in preparation of tissue regenerative repair agents.

In one embodiment of the present disclosure, in use, the injectable in situ pore-forming hydrogel system is crosslinked at a tissue regenerative repair site to form a porous hydrogel.

In one embodiment of the present disclosure, a method of crosslinking the hydrogel is one of chemical crosslinking, physical crosslinking, and chemical-physical mixed crosslinking.

In one embodiment of the present disclosure, the method of crosslinking is one or more of ionic crosslinking, temperature control, acid-base reaction, photoinitiation, and polymerization reaction. Specifically, ionic crosslinking means using an aqueous solution containing one of calcium ions, zinc ions, strontium ions, divalent iron ions, tripolyphosphate ions, sulfate ions, citrate ions as the crosslinking agent; temperature control means cooling by a deionized water bath with a temperature of 4-25° C. or heating by a deionized water bath with a temperature of 37° C.; acid-base reaction means using hydrochloric acid or sodium hydroxide aqueous solution as the crosslinking agent; photoinitiation means using UV light with a wavelength greater than 300 nm to initiate the crosslinking reaction, or with the aid of 1-[4-(2-hydroxyethoxy)-phenyl]-2-hydroxy-2-methylacetone (Irgacure 2959) or 2,2-dimethoxy-2-phenylacetophenone (Irgacure 651) as a photoinitiator; polymerization reaction means using one of glyoxal, polyacrylic acid, polyethylene glycol, oxalic acid, 8-glycerol phosphate, genipin, and water-soluble carbodiimide as the cross-linking agent.

In one embodiment of the present disclosure, a duration of the cross-linking is from 10 s to 30 min. This duration coincides with an operable time of the tissue to be repaired, allowing the injectable in situ pore-forming hydrogel system of the present disclosure to be used as a repair agent for the tissue.

In one embodiment of the present disclosure, the injectable in situ pore-forming hydrogel system has a modulus of elasticity of 0.1 kPa to 100 kPa and a water content of more than 80 wt % after crosslinking and reaching a swelling equilibrium.

In one embodiment of the present disclosure, an average diameter of pore structures formed after cross-linking of the injectable in-situ pore-forming hydrogel system is from 100 μm to 300 μm and/or a maximum diameter of the pore structures is 500 μm.

In one embodiment of the present disclosure, the porous hydrogel has a porosity of not less than 50%. Preferably, the porosity of the porous hydrogel is from 50% to 80%.

The above technical solution of the present disclosure solves the difficulties of preparing porous structures in injectable hydrogel that encapsulates live cells, and proposes to add magnesium particles to the hydrogel, using hydrogen gas foaming produced by degradation of magnesium particles in contact with water to make pores, with the gas forming around the magnesium particles, gradually expanding and fusing with each other, and finally breaking through the gel's confinement and escaping, leaving porous structures in the gel that are interconnected and connected to the outside. This method is feasible and universal in hydrogel, which usually has a high water content, and the reaction is mild, requires no additional conditions, and is friendly to live cells. In addition, the magnesium ions generated from the degradation of the magnesium particles help cell proliferation and differentiation, and promote osteogenesis and vascularization, making the hydrogel bioactive at the same time.

The above technical solution of the present disclosure has the following beneficial effects:

(1) The porous injectable hydrogel system formed by the pore-forming of the magnesium particles has a porous structure, which is conducive to the rapid infiltration of oxygen and nutrients, thus facilitating the growth of surrounding vascular tissue, effectively improving the survival rate of cells encapsulated in the gel, providing a new technical solution to the problem of low survival rate of cells in the field of regenerative repair research.

(2) The present disclosure provides a simple pore-forming method, which is concise in steps, has no toxic substances introduced, and is friendly to live cells.

(3) The present disclosure utilizes both the injectability of hydrogel and its porous structures, which is important for the repair of cavitary, surgically difficult and irregularly defective tissues; meanwhile, magnesium particles generate magnesium ions after the former undergoes gas production and degradation, which can improve the bioactivity of the gel and aid in tissue repair, and has an osteoinductive effect on stem cells, which can promote new bone formation and is applicable in bone defect repair.

DETAILED DESCRIPTION

The following describes the implementation of the present disclosure through specific examples, and those skilled in the art can easily understand other advantages and effects of the present disclosure from the content disclosed in this specification.

Before further describing specific embodiments of the present disclosure, it should be understood that the scope of protection of the present disclosure is not limited to the specific embodiments described below; it should also be understood that the terms used in the embodiments of the present disclosure are intended to describe specific embodiments and are not intended to limit the scope of protection of the present disclosure. Testing conditions not indicated in the following embodiments are generally in accordance with conventional conditions, or in accordance with the conditions recommended by the respective manufacturer.

When a range of values is given in the embodiments, it is to be understood that both endpoints of each range of values, and any of the values between the two endpoints, may be chosen unless otherwise stated in the present disclosure. Unless otherwise defined, all technical and scientific terms used in the present disclosure have the same meaning as commonly understood by those skilled in the art. In addition to the specific methods, apparatus, and materials used in the embodiments, any method, apparatus, and material of the prior art similar to or equivalent to the methods, apparatus, and materials described in the embodiments of the present disclosure may be used to implement the present disclosure according to the mastery of the prior art and the documentation of the present disclosure by a person skilled in the art.

Embodiment 1

This embodiment concerns the preparation and characterization of a porous injectable hydrogel system formed by pore formation of magnesium particles.

Step 1, Use Magnesium Particles as a Pore-Forming Agent to Prepare Porous Injectable Hydrogel Preparation of type I rat tail collagen: prepare 300 μL×3 mg/mL of the collagen, 50 μL 10×PBS, 81 μL dH$_2$O, and 69 μL×0.1 mol/L NaOH solution, add magnesium particles, then mix, and leave at room temperature to form the gel.

Figure 1:
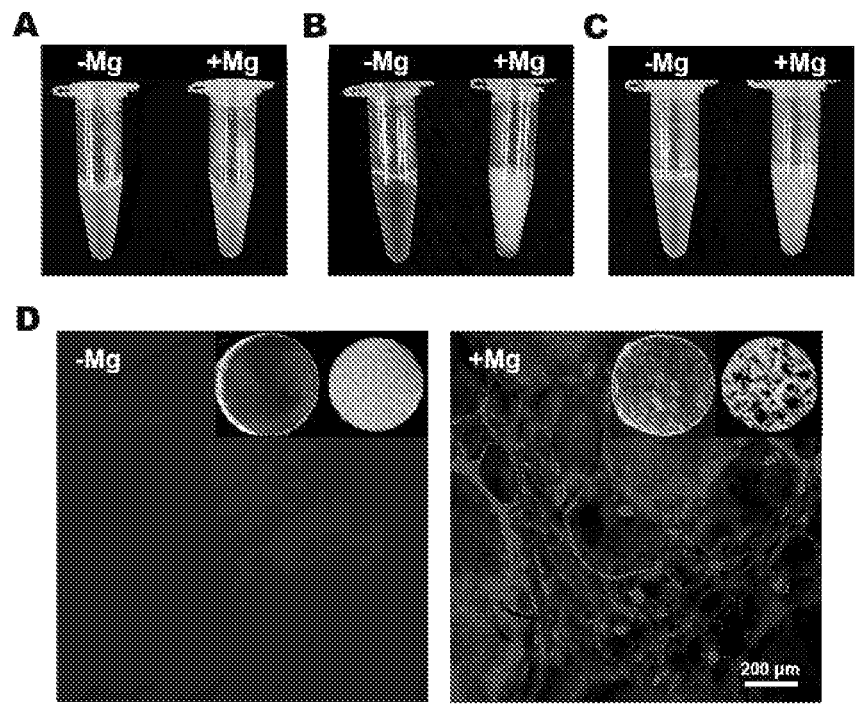
FIG. 1 shows porous structures formed by pore-forming by magnesium particles in a variety of hydrogels as characterized by stereomicroscopy and X ray imaging, along with enlarged stereomicroscopy images to show pore penetration. Among them, A is type I collagen, which is formed into gel by acid-base reaction; B is gelatin, which is formed into gel by cooling; C is silk protein, which is cross-linked by chemical polymerization reaction; D is sodium alginate (alizarin red staining), which is cross-linked by calcium ion.

The corresponding experimental result is shown in FIG. 1A. Compared with the control group, the added magnesium particles can generate pores within the gel while collagen gelling.

Warm up 15% (w/v) gelatin solution to 37° C. in a water bath, mix it with magnesium particles, and cool the mixture down to 25° C. (room temperature) to form gels.

The corresponding experimental result is shown in FIG. 1B. Compared with the control group, the added magnesium particles can generate pores within the gel while gelatin gelling.

Prepare 8% (w/v) silk fibroin solution, 0.5 wt % H$_2$O$_2$ solution, and 1 kU horseradish peroxidase at a volume ratio of 1000:20:20, add magnesium particles and mix, and leave to gel at 37° C. for 5-10 min.

The corresponding experimental result is shown in FIG. 1C. Compared with the control group, the added magnesium particles can generate pores within the gel while silk fibroin gelling.

Prepare 15% (w/v) gelatin solution and 4% (w/v) sodium alginate solution using 0.5% (w/v) NaCl solution as the solvent. Mix the 15% gelatin solution, the 4% sodium alginate solution, and 1 mg/mL alizarin red solution at a volume ratio of 3:2:1, add magnesium particles and mix, pour the resultant solution into a cylindrical mold, and perform cross-linking with 0.1 mol/L CaCl$_2$ solution. The gel was demolded and observed with a stereomicroscope and x-ray films were taken.

The corresponding experimental result is shown in FIG. 1D. Inside the gelatin-sodium alginate gel, magnesium particles can help form multi-level porous structures with pores connecting with each other.

Step 2: Optimization of Parameters Using Magnesium Particles as Pore-Forming Agent Equal amounts of ground chip magnesium particles with a particle size of 100 μm, and atomized spherical magnesium particles with particle sizes of 20 μm, 50 μm, and 100 μm were added into the gelatin-sodium alginate solution prepared in step 1, respectively, and molds and gelling method were the same as in step 1. MicroCT scan and reconstruction were performed after gel demoulding.

Figure 2:
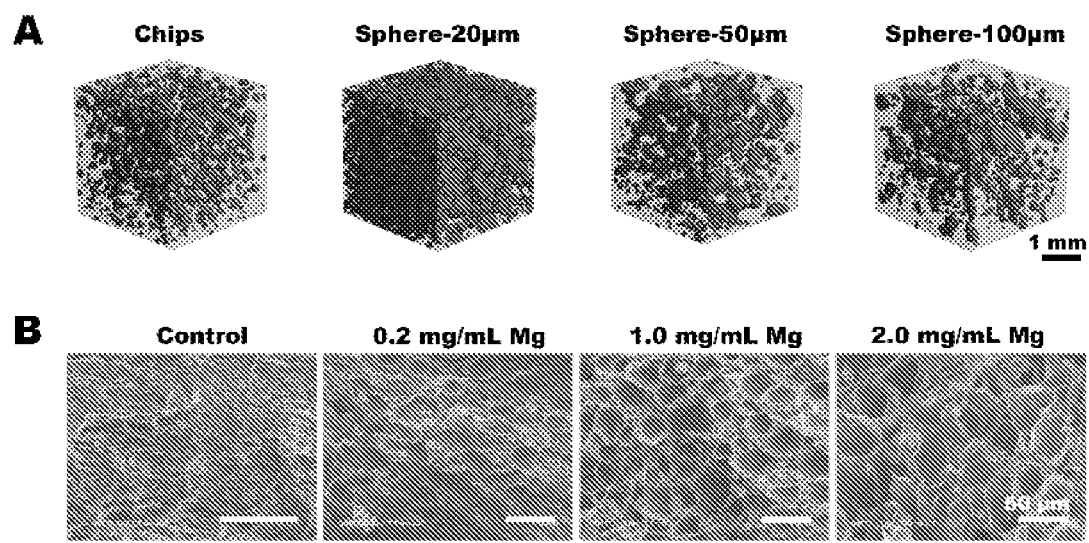
FIG. 2 shows the pore formation in a gelatin-sodium alginate injectable hydrogel system by magnesium particles with different sizes and different added amounts. Among them, A shows the pore formation by magnesium particles with a same added amount and different particle sizes (100 μm chip magnesium particles, and 20 μm, 50 μm, and 100 μm atomized spherical magnesium particles, respectively), as characterized by MicroCT; and B shows the pore formation by magnesium particles with a same particle size and different added amounts (0, 0.2 mg/mL, 1.0 mg/mL, and 2.0 mg/mL), as characterized by SEM.

The corresponding experimental result is shown in FIG. 2A. Compared with magnesium particles of other sizes, the gel porosity of atomized spherical magnesium particles with a particle size of 20 μm in the gelatin-sodium alginate hydrogel mixture is the highest.

Add the atomized spherical magnesium particles with a particle size of 20 μm into the gelatin-sodium alginate mixture in step 1 at 0.2, 1.0, and 2.0 mg/mL, respectively, and add no magnesium particles to the control group, using same molds and gelling method as in step 1. Place the gel in liquid nitrogen for 30 min for rapid freezing after demolding, take the gel out, and evacuate the gel in a freeze dryer for 4 h, after a dried sample is obtained, spray the gel with gold, and characterize the sample with field emission scanning electron microscopy, scanning 50× and 100× field of view.

The corresponding experimental result is shown in FIG. 2B. The internal porosity of the gelatin-sodium alginate mixed hydrogel increases with the increase of added magnesium particles, where pores formed by 1 mg/mL addition of magnesium particles are more homogeneous, with pore sizes in the range of 100-300 μm.

Embodiment 2

In this embodiment, a porous hydrogel with pores made of magnesium particles was used to improve cell survival rate.

Step 1, Porous Hydrogel is Prepared Using Magnesium Particles as a Pore-Forming Agent to Improve Cell Survival In Vitro Prepare 15% gelatin solution and 4% sodium alginate solution. Mix 15% gelatin solution, 4% sodium alginate solution and 3T3-L1 cell suspension at a volume ratio of 3:2:1, with a final cell concentration of $10^6$-$10^7$/m L. The experimental group was added with magnesium particles for mixing, and the control group was added with no magnesium particles, the gels were cross-linked in 0.1 mol/L CaCl$_2$ solution, with a volume of 150 μL per sample. The cells were cultured in vitro for 1, 3 and 7 days, stained with live-dead double staining kit, and the number of green and red cells were observed by fluorescence microscopy.

Figure 3:
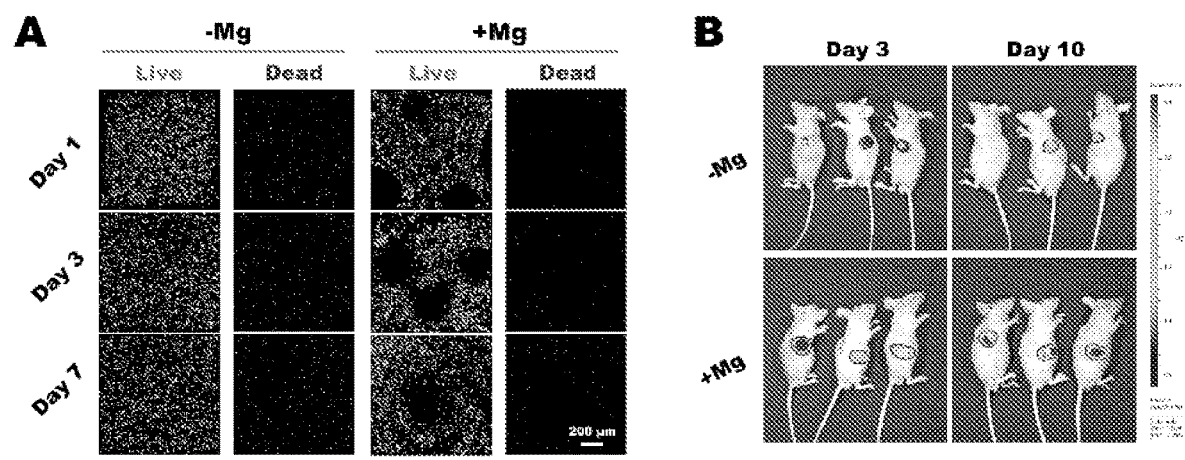
FIG. 3 shows a study result concerning encapsulating live cells in porous hydrogel obtained from the pore formation by magnesium particles and an improved survival rate of the live cells. In A, gelatin-sodium alginate gel-encapsulated 3T3-L1 cells were cultured in vitro, and the effect of the pore formation by magnesium particle on cells' survival rates in vitro was examined by live-dead double staining; in B, gelatin-sodium alginate gel-encapsulated and Luciferase and GFP double-labeled cells were implanted subcutaneously in nude mice, and the effect of pore formation by magnesium particle on cells' survival rates in vivo was evaluated by live fluorescence imaging.

The corresponding experimental result is shown in FIG. 3A. This in vitro culture result shows that the use of magnesium particles in the cell-containing hydrogel for in situ pore-forming does not cause more cell deaths; rather, the porous structure facilitates cell survival, which is significantly different from the control group.

Step 2: Porous Injectable Hydrogel is Prepared Using Magnesium Particles as a Pore-Forming Agent to Improve Cell Survival In Vivo Construct LV-EF1A>Luciferase-CMV>EGFP/T2A/Puro lentiviral vector and transfect 3T3-L1 cells with the vector. Perform fluorescence microscopy to observe the expression of green fluorescent protein to detect the efficiency of cell transfection. Amplify Luciferase and GFP double-labeled cells. Prepare 15% gelatin solution and 4% sodium alginate solution. Mix 15% gelatin solution, 4% sodium alginate solution and the above cell suspension at a volume ratio of 3:2:1, with a final cell concentration of $10^6$-$10^7$/mL. The experimental group was added with magnesium particles for mixing, and the control group was added with no magnesium particles, the gels were cross-linked in 0.1 mol/L $CaCl_2$ solution, with a volume of 150 μL per sample. The above cell-containing gel samples were implanted subcutaneously on the back of nude mice; and at the 3rd day and the 10th day, fluorescein potassium salt was injected intraperitoneally into each nude mouse at 150 mg/kg, 15 min later the nude mice were anesthetized by injection, and then fluorescence intensity was analyzed by in vivo imaging.

The corresponding experimental result is shown in FIG. 3B. The in vivo fluorescence imaging shows that the cells implanted in vivo with the gel have a higher survival rate and can proliferate in the experimental group (with pore formation of magnesium particles), indicating that the effect of magnesium particles for pore formation to promote cell survival can be maintained in vivo.

Embodiment 3

Use of porous injectable hydrogel with pores made of magnesium particles to promote ingrowth of blood vessels and tissues.

Mix 15% gelatin solution, 4% sodium alginate solution, and 0.5% NaCl solution at a volume ratio of 3:2:1. The experimental group was added with magnesium particles for mixing, the control group was added with no magnesium particles; subcutaneously inject the gel into the back of eight-week-old male SD rats, 200 μL of each sample. The gels were cross-linked with 0.1 mol/L $CaCl_2$ solution after injection, and saline was used for rinsing and washing for three times. Perform cannulation and Microfil vascular perfusion for descending aortic. Samples were taken, fixed, and scanned with MicroCT, and 3D reconstruction was performed to analyze the amount of vessels. Samples were paraffin-embedded after scanning, sectioned, HE stained, and statistically analyzed for tissue ingrowth.

Figure 4:
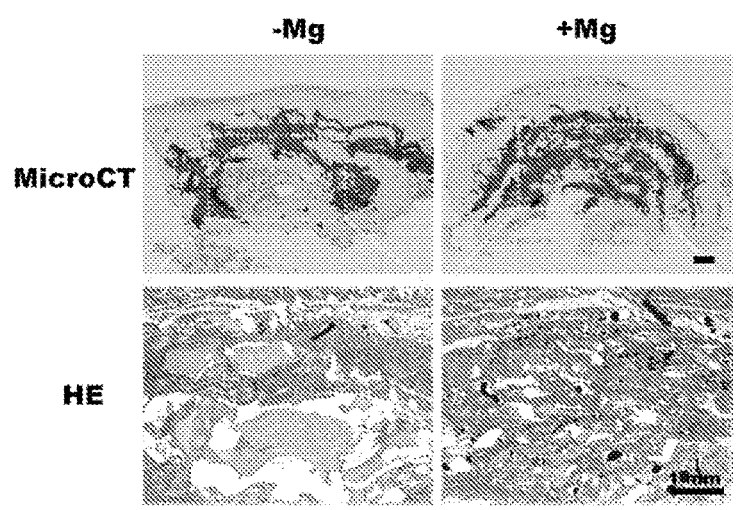
FIG. 4 shows an experimental effect where a hydrogel system with pores made by magnesium particles facilitates the growth of surrounding vessels and tissues, with Microfil perfusion performed before MicroCT scanning to assess the amount of vessel ingrowth, and HE staining of sections to observe the amount of tissue ingrowth.

The corresponding experimental result is shown in FIG. 4. In the experimental group (with porous gel obtained from pore-forming by magnesium particles), the amount of peripheral vessels and the amount of tissue ingrowth are significantly higher than those in the control group (without porous structures).

Embodiment 4

Stem cells encapsulated in porous hydrogel with pores made of magnesium particles are used to promote vascularized bone regeneration.

Step 1. Isolation and Culture of Rat Bone Marrow Stem Cells (rBMSCs)

4-week-old SD rats were sacrificed by cervical dislocation, bilateral femurs and tibias were separated under aseptic conditions, and bilateral metaphysis were cut off; bone marrow cavities were repeatedly rinsed with DMEM culture medium, and the rinsate was collected and centrifuged at 1000 rpm for 15 min at room temperature, and the supernatant is discarded; then the cells were resuspended and incubated on plates.

Step 2: Preparation of Gel Containing rBMSCs

15% gelatin solution, 4% sodium alginate solution and 2-4 generations of rBMSCs cell suspension were mixed at a volume ratio of 3:2:1, and the final concentration of cells was $10^6$-$10^7$/m L.

Step 3: Preparation and Repair of Bone Defect Model

A cylindrical defect with a diameter of 2.5 mm and a depth of 3 mm was created on the medial side of the distal femur of eight-week-old male SD rats after anesthesia. In the experimental group, magnesium particles were added to the gel-cell mixture, and in the control group, no magnesium particles were added. The defects were injected with the gel-cell mixture, 30 μL of each sample. The gels were cross-linked with 0.1 mol/L $CaCl_2$ solution after injection. Saline were used for rinsing lightly. A blank control group was provided. After 3 weeks, the rats were sacrificed. Samples were taken and fixed, and the new bones were analyzed by MicroCT scanning and 3D reconstruction.

Figure 5:
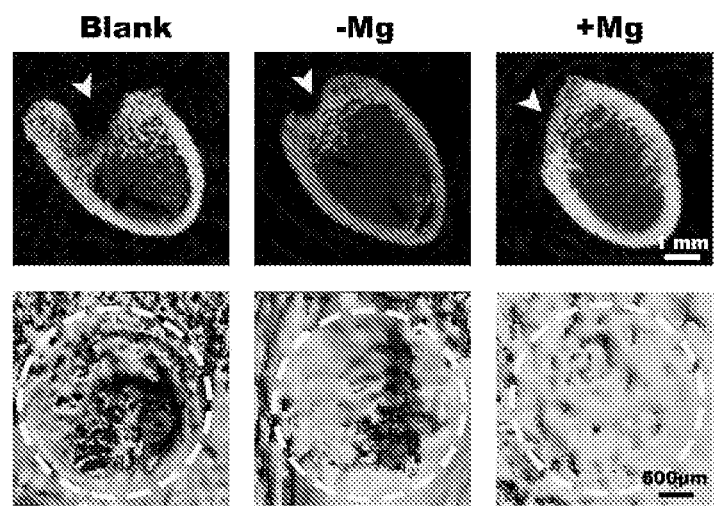
FIG. 5 shows an experimental effect where a hydrogel system with pores made by magnesium particles facilitates vascularized bone regeneration and repair, with rat bone marrow MSCs encapsulated in sodium alginate-gelatin gel to repair rat femoral distal defects, and the osteogenesis was assessed by MicroCT.

The corresponding experimental result is shown in FIG. 5, defective bone repaired with the porous gel containing magnesium shows the best regeneration result, which is significantly different from the blank control group and the group without magnesium particles.

Embodiment 5

In situ pore-forming using magnesium particles in a hydrogel encapsulating stem cells to improve defect repair.

Step 1. Isolation and Culture of Rat Bone Marrow Stem Cells (rBMSCs)

4-week-old SD rats were sacrificed by cervical dislocation, bilateral femurs and tibias were separated under aseptic conditions, and bilateral metaphysis were cut off; bone marrow cavities were repeatedly rinsed with DMEM culture medium, and the rinsate was collected and centrifuged at 1000 rpm for 15 min at room temperature, and the supernatant was discarded; then the cells was resuspended and incubated on plates.

Step 2: Preparation of Injectable Gel Containing Magnesium Particles

15% gelatin solution, 4% sodium alginate solution, 2-4 generations of rBMSCs cell suspension or saline were mixed at a volume ratio of 3:2:1, the final concentration of cells was $10^6$-$10^7$/m L, and the concentration of added magnesium particles was 1.0 mg/mL.

Step 3: Preparation and Repair of Bone Defect Model

In eight-week-old male SD rats, circular defects with a diameter of 2.5 mm and a depth of 1 mm were created on the proximal medial side of tibia after anesthesia. The experimental group is a gel-cell mixture containing magnesium particles, and the control group is gel containing magnesium particles without stem cells. The defects were injected with the gel-cell mixture, 20 μL of each, the gels were cross-linked in 0.1 mol/L $CaCl_2$ solution after injection, and then saline were used for rinsing lightly. After 2 weeks, the rats were sacrificed, samples were taken and fixed, and the new bones were analyzed by MicroCT scanning and 3D reconstruction. The samples were paraffin-embedded, sectioned, HE stained, and statistically analyzed for new bone growth.

Figure 6:
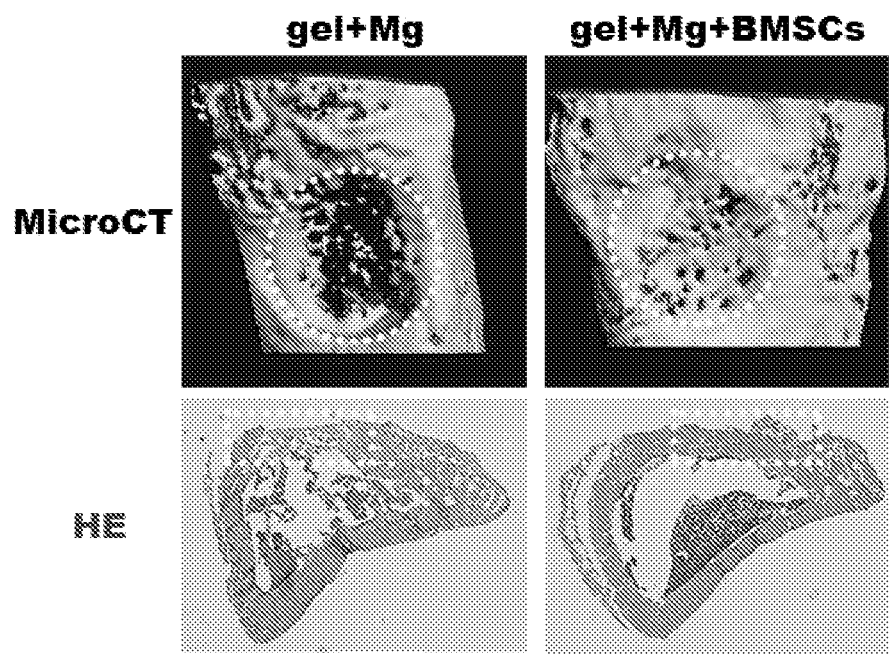
FIG. 6 shows an experimental effect where the pore formation of magnesium particles in a hydrogel system encapsulating live cells facilitates bone defect repair, with the magnesium particles added to sodium alginate-gelatin gel with or without rat bone marrow MSCs to repair rat tibial defects, and osteogenesis assessed by MicroCT and HE staining of sections.

The corresponding experimental result is shown in FIG. 6. Compared with the porous hydrogel without cells, the use of magnesium particles for in situ pore formation in the hydrogel encapsulating live cells can effectively improve the bone regeneration effect.

In summary, the present disclosure is based on the principle of degradation and gas production of magnesium particles to prepare a live-cell-loaded, injectable, in situ pore-forming, bioactive hydrogel, and the in vitro and in vivo survival rates of the cells encapsulated in the gel were examined; and the effect of the gel on promoting tissue regeneration and repair was tested in a rat bone defect model. The results show that the internal porous structures of the gel formed by the degradation of magnesium particles can facilitate the infiltration of oxygen and nutrients, and improve the survival rate of stem cells; at the same time, the porous structures are also conducive to inducing the rapid growth of external tissue vessels, accelerating the vascularization process; in addition, the magnesium ions generated by the degradation of magnesium particles in vivo act on stem cells, promoting the proliferation and differentiation of osteogenic cells, accelerating the formation of new bone and promoting the repair of bone defects.

The above-mentioned embodiments only exemplarily illustrate the principles and effects of the present disclosure, but are not used to limit the present disclosure. Any person skilled in the art may modify or change the above embodiments without violating the spirit and scope of the present disclosure. Therefore, all equivalent modifications or changes made by those skilled in the art without departing from the spirit and technical concepts disclosed by the present disclosure should still be covered by the attached claims of the present disclosure.

What is claimed is:

1. An injectable in situ pore-forming hydrogel system, wherein the injectable in situ pore-forming hydrogel system uses an injectable hydrogel as a continuous base phase, and isolated live cells and magnesium particles are distributed in the continuous base phase, wherein the injectable hydrogel is a precursor or prepolymer of hydrogel, which forms hydrogel by cross-linking, wherein the injectable hydrogel is a precursor or prepolymer of a hydrogel selected from the group comprising alginate, gelatin, agarose, chitosan, collagen, silk fibroin, cellulose, glucose, hyaluronic acid, chondroitin sulfate, polyvinyl alcohol, polyethylene glycol, and derivatives thereof, wherein the isolated live cells are one or more of mesenchymal stem cells, embryonic stem cells, and induced multifunctional cells, wherein an amount of the magnesium particles in the injectable in situ pore-forming hydrogel system is 0.2 mg to 2.0 mg of the magnesium particles per 1 mL of the injectable in situ pore-forming hydrogel system, wherein the injectable in-situ pore-forming hydrogel system has one or two of the following two features: the magnesium particles have an average particle size of 20 µm to 100 µm; the magnesium particles have a maximum particle size of 150 µm, wherein a mass fraction of the magnesium element in the magnesium particles is above 99.98%, wherein a concentration of the isolated live cells in the injectable in situ pore-forming hydrogel system is $10^6$-$10^7$ cells per mL.

2. A method for preparing the injectable in situ pore-forming hydrogel system as claimed in claim 1, which comprises mixing the injectable hydrogel, the isolated live cells, and the magnesium particles.

3. A method of using the injectable in situ pore-forming hydrogel system as claimed in claim 1 in the preparation of a tissue regenerative repair agent, comprising forming a porous hydrogel by crosslinking of the injectable in situ pore-forming hydrogel system at a tissue regenerative repair site.

4. The method according to claim 3, wherein a method of crosslinking the hydrogel is one of chemical crosslinking, physical crosslinking, and chemical-physical mixed crosslinking.

5. The method according to claim 4, wherein the method of crosslinking is one or more of ionic crosslinking, temperature control, acid-base reaction, photoinitiation, and polymerization reaction.

6. The method according to claim 3, wherein a duration of the crosslinking is from 10 s to 30 min.

7. The method according to claim 3, wherein the injectable in situ pore-forming hydrogel system has a modulus of elasticity of 0.1 kPa to 100 kPa and a water content of more than 80 wt % after crosslinking and reaching a swelling equilibrium.

8. The method according to claim 3, wherein an average diameter of porous structures formed after cross-linking of the injectable in-situ pore-forming hydrogel system is from 100 µm to 300 µm and/or a maximum diameter of the porous structures is 500 µm.

9. The method according to claim 3, wherein the porous hydrogel has a porosity of at least 50%.

* * * * *